(12) United States Patent
Wang

(10) Patent No.: US 9,149,217 B1
(45) Date of Patent: Oct. 6, 2015

(54) APPARATUS MONITORING SIGNAL IN SITU

(71) Applicant: Wei-Kung Wang, Taipei (TW)

(72) Inventor: Wei-Kung Wang, Taipei (TW)

( * ) Notice: Subject to any disclaimer, the term of this patent is extended or adjusted under 35 U.S.C. 154(b) by 0 days.

(21) Appl. No.: 14/677,257

(22) Filed: Apr. 2, 2015

Related U.S. Application Data

(63) Continuation-in-part of application No. 14/327,485, filed on Jul. 9, 2014, which is a continuation-in-part of application No. 12/173,275, filed on Jul. 15, 2008, now abandoned, which is a continuation-in-part of application No. 10/924,021, filed on Aug. 23, 2004, now abandoned, which is a continuation-in-part of application No. 10/123,124, filed on Apr. 16, 2002, now abandoned, which is a continuation-in-part of application No. 09/766,237, filed on Jan. 19, 2001, now abandoned.

(30) Foreign Application Priority Data

Mar. 17, 2000 (TW) ................................ 89104938 A
Aug. 27, 2003 (TW) .............................. 092123724 A

(51) Int. Cl.
*A61B 5/00* (2006.01)
*A61B 5/1455* (2006.01)
*A61B 5/145* (2006.01)

(52) U.S. Cl.
CPC ......... *A61B 5/14552* (2013.01); *A61B 5/14532* (2013.01); *A61B 5/14546* (2013.01); *A61B 5/6826* (2013.01); *A61B 5/6838* (2013.01)

(58) Field of Classification Search
CPC ............. A61B 5/14552; A61B 5/6838; A61B 5/6826; A61B 5/14546; A61B 5/14532; A61B 5/1455
USPC ................................... 600/309, 322, 323, 324
See application file for complete search history.

(56) References Cited

U.S. PATENT DOCUMENTS

| | | | |
|---|---|---|---|
| 4,685,464 A * | 8/1987 | Goldberger et al. | 600/344 |
| 7,333,186 B2 * | 2/2008 | Oshima et al. | 356/39 |
| 2002/0173709 A1 * | 11/2002 | Fine et al. | 600/335 |
| 2013/0211264 A1 * | 8/2013 | Lamego | 600/479 |

* cited by examiner

*Primary Examiner* — Max Hindenburg
*Assistant Examiner* — Jonathan M Foreman
(74) *Attorney, Agent, or Firm* — patenttm.us

(57) ABSTRACT

For repeatedly measuring signals from a fixed position of a tissue to monitor the blood composition, a subject adaptor is used to secure the subject position and a position fixing device uses a remote sensing tool to detect the subject position. The subject adaptor and the position fixing device are used to guide the moving of the subject relative to a position of the last measurement of a first signal analyzer. The signals can be from an aggregate of the designated composition with the other ingredients of the blood.

12 Claims, 3 Drawing Sheets

APPARATUS MONITORING SIGNAL IN SITU

CROSS-REFERENCE TO RELATED APPLICATIONS

This is a continuation-in-part of a continuation-in-part application of application Ser. No. 14/327,485, now pending, which is a continuation-in-part application of application Ser. No. 12/173,275 filed on Jul. 15, 2008, now abandoned, which is a continuation-in-part application of copending application Ser. No. 10/924,021 filed on Aug. 23, 2004, entitled "AN APPARATUS MONITORING SIGNAL IN SITU", now abandoned, which is a continuation-in-part application of application Ser. No. 10/123,124 filed on Apr. 16, 2002, now abandoned, which is a continuation-in-part application of application Ser. No. 09/766,237 filed on Jan. 19, 2001, now abandoned, and claims the benefit thereof and incorporates the same by reference.

BACKGROUND OF THE INVENTION (A) Field of the Invention
This invention relates to a medical device and blood composition sampling.
(B) Description of Related Art
U.S. application Ser. Nos. 10/123,124 and 10/207,610

SUMMARY OF THE INVENTION

There is a need to repeatedly measure the most important physiological parameters, such as blood sugar, blood oxygen and cholesterol, in order to monitor the variations thereof. For such a purpose, it is provided with a first signal generator in the tissue, for example, a radio-isotope in the tissue emits a signal such as .alpha., .beta., .gamma. particles. Also, the signal can be an electromagnetic wave (visible light, UV, IR, X-ray, microwave) from outside the tissue. After the tissue is irradiated, absorption, scattering, fluorescence, etc., are induced in the tissue. A first signal analyzer or a spectrum analyzer may be used to monitor the concentration of ingredients in the tissue through monitoring an induced signal from the tissue. The induced signal may not be from the ingredient itself. The induced signal may also be from an aggregate of the ingredient with some other specific component, such as Aggregate ⟷ ingredient (to be measured)+specific component.

In the invention, glucose and hemoglobin are used as an example.

Hemoglobin+glucose. ⟷ HbA1c (precursor) ⟷ HbA1c

Before hemoglobin and glucose become a compound HbA1c, there is an intermediate stage of aggregate HbA1c (precursor). As the concentration of Hb is somewhat stable, the concentration of glucose in the blood may be figured out from the signal of HbA1c (precursor).

To fix the tissue at the same position for sequential measurements, a subject adaptor is invented. The subject adaptor works better with an extruded tissue, such as a finger or toe. If there is a cone-shaped guide inside the subject adaptor, it guides the finger to anchor at the top of the cone-shaped guide in operation. To secure the finger in a stretched position and at the right angle, soft pads both above and below the finger can be used. These soft pads could be replaced with one or more elastic membranes which are stretched to wrap around the finger and hold the finger smoothly and softly so that no blood circulation is interfered. These pads or membranes can be in a concaved slot. The above entire structure is called the subject adaptor. One or more springs can be used to hold the subject adaptor to improve its adaptability.

To keep the finger at the same position as the last measurement, a method to sense the position information of the finger is needed, and then this position information is used to move the finger back to the same relative position with respect to the first signal analyzer. Here a few remote sensing methods to sense the position of the finger are disclosed.

The position of the finger is detected by changing signal intensity of a second signal by using a second signal generator and a second signal analyzer, and the second signal generator and the second signal analyzer can be mounted on the same side of the finger. The second signal generator generates and outputs the second signal to the finger. In this way, the second signal analyzer collects a scattered light from the finger. This scattered light changes along the finger due to natural marker such as a nail and a skin border. There will be a huge scattering light fluctuation due to irregular and anatomical structure. Or an artificial marker may be put somewhere along the finger which can be dark color, light reflection, or irregular surface, and all artificial markers will change the scattering light of the second signal significantly to be used to identify the position of the finger.

The second configuration can be that the second signal generator and the second signal analyzer are at the opposite directions of the finger. The second signal generator and the second signal analyzer may rotate around the finger. A horizontal position is shown in FIGS. 3 and 4. When the finger tip starts to block the signal output from the second signal generator to enter the second signal analyzer, the position of the finger is known.

Further, using a see through window, this method uses image or direct eye contact to see the position of the finger, and then adjust the position of the finger to the same position as the last measurement. This structure is especially useful for a clamp like finger adaptor that has the first signal generator and the first signal analyzer, such as pulsatile oxygenometer that is used for measuring oxygen concentration in the blood. On the clamp, a see through window can be opened, so that the finger can be seen when the clamp is applied to the finger. There are scales on the see through window along side with the finger, so that where the finger is can be seen when the next measurement to make sure that the finger is at the same position according to the scale is made. This see through window is at the top of the clamp and is corresponding to the tip of the finger.

When the clamp is put on the finger, where the finger tip is can be seen clearly. Because the first signal generator and the first signal analyzer are away from the finger tip, this see through window will not interfere with the mechanism of measuring the oxygen content. What needs to be done is cover this see through window with signal blocking cover, so that, no leaking signal will enter the clamp to interfere with readings of the finger adaptor.

To improve the precision of positioning the finger, a patient's palm may be placed on a flat pad, so that the finger does not rotate due to incorrect posture.

DETAILED DESCRIPTION OF THE INVENTION

Figure 1:
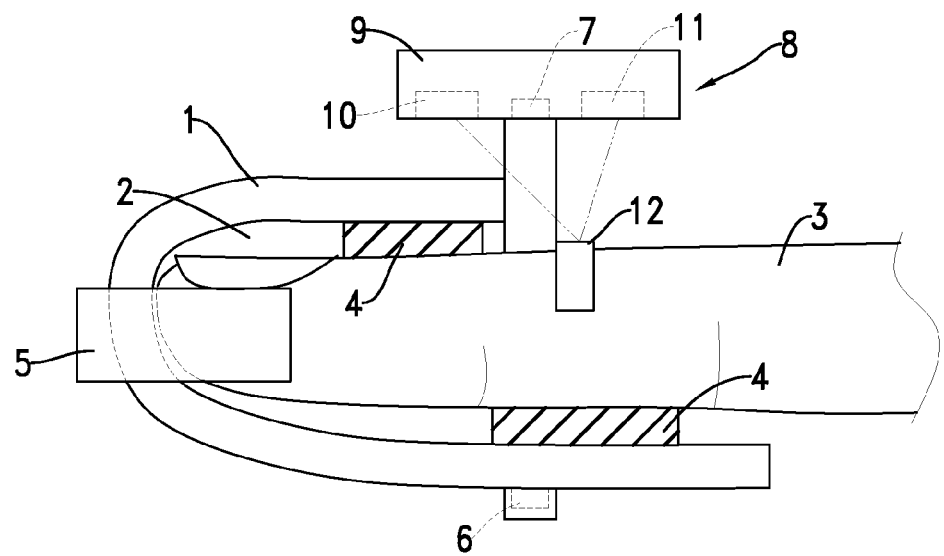
FIG. 1 is a cross-sectional view of a first embodiment of the apparatus for monitoring a signal in situ of the present invention.
Figure 2:
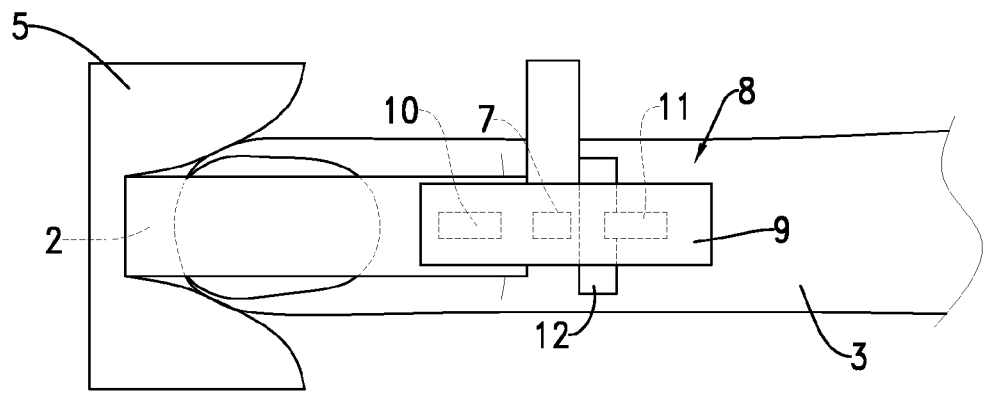
FIG. 2 is a top view of the first embodiment of the apparatus for monitoring a signal in situ of the present invention as shown in FIG. 1.

FIGS. 1 and 2 respectively are a cross-sectional view and a top view of a first embodiment of the apparatus for monitoring a signal in situ of the present invention. The apparatus comprises a subject adaptor 1 for securing a subject for repeated measurements during repeated insertions. The subject adaptor 1 comprises a concaved slot 2, multiple soft pads 4, and a cone-shaped guide 5. The concaved slot 2 is made with a mold in the shape of an extruded tissue, here a finger 3. The concaved slot 2 and the finger 3 are complementary in shape. The soft pads 4 are located inside the concaved slot 2 and both above and below the finger 3 so as not to interfere with signals. The cone-shaped guide 5 is located at the distal end inside the concaved slot 2 to insure the correct position of the finger 3. The apparatus further has a first signal generator 6 and a first signal analyzer 7. The first signal generator 6 is positioned under the finger 3, for generating a signal to be transmitted to a fixed position of the finger 3 via a hole through the subject adaptor 1 and one of the soft pads 4. The first signal analyzer 7 is positioned opposite to the first signal generator 6 with respect to the finger 3, for receiving and analyzing an induced signal from the fixed position of the finger 3 (i.e. for receiving and analyzing an induced signal from the finger 3 in situ). The first signal generator 6 and the first signal analyzer 7 are connected together in order to fix their relative position. The position of the first signal generator 6 and the first signal analyzer 7 may be exchanged. Therefore, the first signal analyzer 7 may be positioned under the finger 3, and the first signal generator 6 may be positioned opposite to the first signal analyzer 7 with respect to the finger 3. With the help of the cone-shaped guide 5, the finger 3 can be fixed in order to make a new measurement on the fixed position of the finger 3 where previous measurements were made. Thereby, repeated measurements, i.e. the so-called "monitoring," could be made on the fixed position of the finger 3 during repeated insertions of the finger 3. It is pointed out in the invention that the induced signal used for composition analysis of a special ingredient is generated by the ingredient-making chemical actions with other ingredients in blood.

To improve the precision of positioning the finger 3, a patient's palm may be placed on a flat pad, so that the finger 3 does not rotate (nor tilt) due to incorrect posture to improve position fixing ability. A position fixing device 8 is disclosed. The position fixing device 8 uses a remote sensing tool to detect the position of the subject, and comprises a moving component 9 to define the position of the finger 3 precisely. The moving component 9 is movably mounted on the subject adaptor 1. In the first embodiment of the apparatus, a terminal of the moving component 9 is attached with a second signal generator 10, a second signal analyzer 11, and the first signal analyzer 7 as described above, and is positioned above the finger 3 and moves relatively to the finger 3. An opposite terminal of the moving component 9 is attached with the first signal generator 6, and is positioned under the finger 3. Besides, when the position of the first signal generator 6 and the position of the first signal analyzer 7 are exchanged, a terminal of the moving component 9 above the finger 3 is attached with the second signal generator 10, the second signal analyzer 11, and the first signal generator 7, and the first signal generator 6 is attached to the opposite terminal of the moving component 9 under the finger 3. The second signal generator 10 generates a second signal, such as light, etc., to be transmitted to a marker 12. The marker 12 can be a natural one such as an edge, a nail and skin border, or a wrinkle of the finger 3, etc., or an artificial one painted or pasted on the finger 3. When the second signal reflected from the marker 12 is detected by the second signal analyzer 11, the second signal informs the apparatus of the position of the marker 12. The apparatus then knows the precise position of the finger 3 and thereby the first signal analyzer 7 attached to the moving component 9 is moved to the position of the last measurement. In this way, the position of the finger 3 may be positioned more precisely.

At the same time when the second signal generator 10 is moving along the finger 3, the second signal detected by the second signal analyzer 11 is recorded as a monitor to detect the rotation or tilt of the finger 3 to further improve the position fixing device 8. At the first measurement the second signals detected by the second signal analyzer 11, is recorded, this recorded second signals are compared with the second signals recorded for the following measurements. If significant difference between the second signals of the first measurement and the second signals of the following measurement is determined, the finger 3 at the following measurement is not at the same position as the first measurement.

The moving component 9 may be driven by a computer controlled motor. A computer saves a position of the last measurement and an original relation between the position of the last measurement and the marker 12. The second signal analyzer 11 and the computer controlled motor are electrically connected to the computer via wired or wireless connection. Once, the second signal analyzer 11 detects a relation between the position of the finger 3 and the marker 12, the computer compares the original relation and the relation detected by the second signal analyzer 11, and then the computer will instruct the computer controlled motor where to go.

Figure 3:
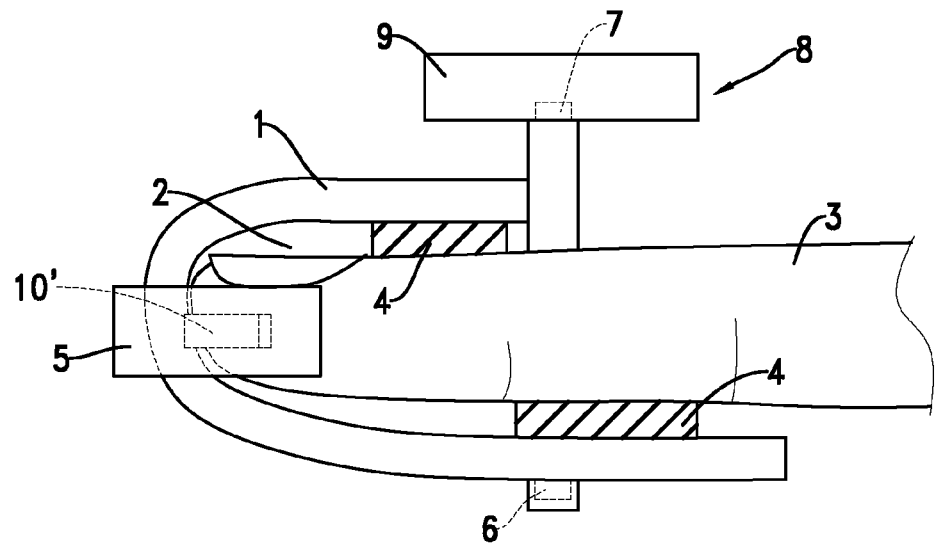
FIG. 3 is a cross-sectional view of a second embodiment of the apparatus for monitoring a signal in situ of the present invention.
Figure 4:
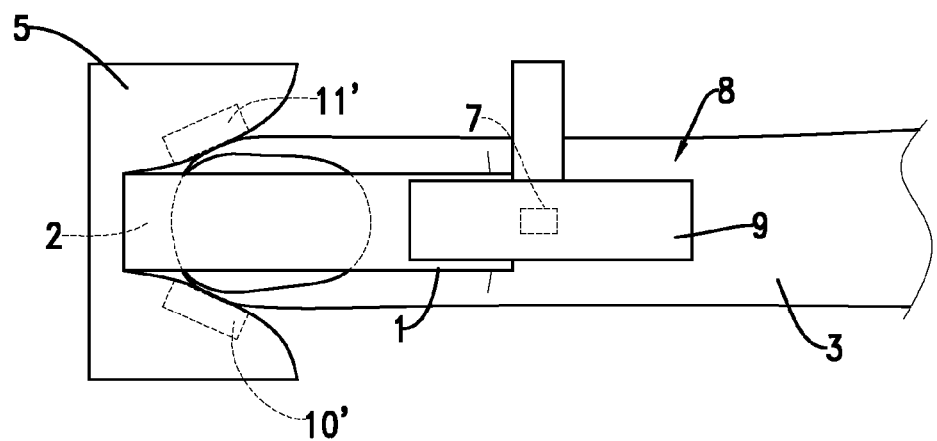
FIG. 4 is a top view of the second embodiment of the apparatus for monitoring a signal in situ of the present invention as shown in FIG. 3.

With reference to FIGS. 3 and 4, a second embodiment of the present invention is same as the first embodiment of FIGS. 1 and 2. But, the moving component 9 is only attached with the first signal generator 6 and the first signal analyzer 7. The second signal generator 10' and the second signal analyzer 11' are around the tip of the finger, and at lateral position of the finger. The marker 12 is the finger tip. In the second embodiment, the second signal generator 10' and the second signal analyzer 11' are mounted on two opposite sides of the cone-shaped guide 5, and are respectively positioned at two opposite sides of the finger tip. When the finger 3 moves into the concaved slot 2 and the finger 3 blocks the signal output from the second signal generator 10', the position of the finger 3 is detected and known. Therefore, the moving component 9 attached with the first signal generator 6 and the first signal analyzer 7 can be moved to the position of the last measurement of the finger 3.

Figure 5:
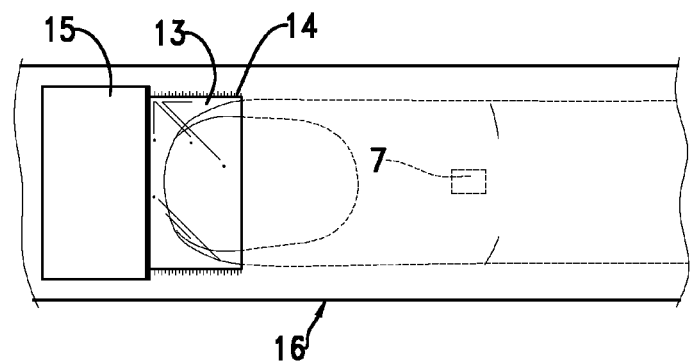
FIG. 5 is a cross-sectional view of a third embodiment of the apparatus for monitoring a signal in situ of the present invention.
Figure 6:
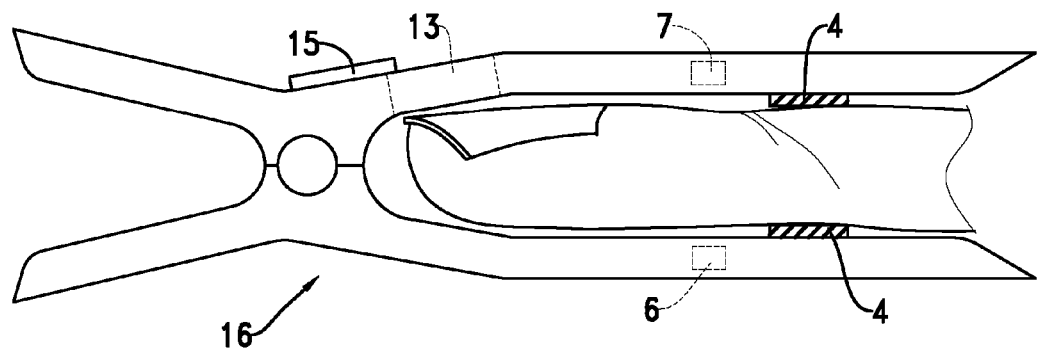
FIG. 6 is a top view of the third embodiment of the apparatus for monitoring a signal in situ of the present invention as shown in FIG. 5.

With reference to FIGS. 5 and 6, the subject adaptor 1 may be a clamp 16. The remote sensing tool further comprises a see through window 13, such as a transparent window, with scales 14 mounted on an upper cover of the clamp 16 and an opaque cover 15, so that the finger 3 may be fixed at the same position of the last measurement according to the see through window 13 and the scales 14. The first signal generator 6 is mounted on a lower cover of the clamp 16, and the first signal analyzer 7 is mounted on the upper cover of the clamp 16. The opaque cover 15 is mounted on the upper cover of the clamp 16 and near the see through window 13, and the opaque cover 15 is not transparent to the signals. After the finger 3 is fixed at a right position, this opaque cover 15 is closed to block the light from entering the inside of the clamp 16. This secures the accuracy of the measurements. In the third embodiment, the opaque cover 15 is a sliding lid.

What is claimed is:

1. An apparatus for monitoring an induced signal in situ comprising:
   a subject adaptor configured to secure a subject in situ during repeated measurements;
   a position fixing device using a remote sensing tool to detect a position of the subject, and comprising a moving component movably mounted on the subject adaptor, wherein the moving component has two terminals;
   a first signal generator attached to one of the two terminals of the moving component, for generating a signal, and capable of transmitting the signal to the subject in situ; and
   a first signal analyzer attached to the other terminal of the moving component, for receiving and analyzing a signal induced from the subject in situ;
   wherein the remote sensing tool comprises a second signal generator and a second signal analyzer both mounted on one of the two terminals of the moving component; and
   wherein the moving component automatically moves to the subject to lead the second signal generator and the second signal analyzer to a fixed position during repeated measurements.

2. The apparatus as claimed in claim 1, wherein the subject adaptor comprises a concaved slot.

3. The apparatus as claimed in claim 2, wherein the subject adaptor further comprises:
   a cone-shaped guide mounted at a distal end inside the concaved slot to insure the position of the subject.

4. The apparatus as claimed in claim 1, wherein the remote sensing tool identifies a marker for detecting the position of the subject.

5. The apparatus as claimed in claim 4, wherein said marker is a natural one or artificial one.

6. The apparatus as claimed in claim 1, wherein said induced signal comprises a signal from blood composition.

7. The apparatus as claimed in claim 6, wherein said blood composition comprises aggregate of blood composition.

8. The apparatus as claimed in claim 1, wherein:
   the second signal generator is capable of generating a plurality of second signals to the subject;
   the second signal analyzer is capable of detecting the second signals reflected from the subject
   when the moving component is moving along the finger to improve the position fixing.

9. An apparatus for monitoring an induced signal in situ comprising:
   a subject adaptor configured to secure a subject in situ during repeated measurements;
   a position fixing device using a remote sensing tool to detect a position of the subject, and comprising a moving component movably mounted on the subject adaptor;
   a first signal generator attached to one of two terminals of the moving component, for generating a signal, and capable of transmitting the signal to the subject in situ; and
   a first signal analyzer attached to the other terminal of the moving component, and for receiving and analyzing a signal induced from the subject in situ;
   wherein the subject adaptor comprises a concaved slot and a cone-shaped guide mounted at a distal end inside the concaved slot to insure the position of the subject: and
   wherein the remote sensing tool comprises a second signal generator and a second signal analyzer mounted on two opposite sides of the cone-shaped guide.

10. An apparatus for monitoring an induced signal in situ comprising:
    a subject adaptor configured to secure a subject in situ during repeated measurements;
    a position fixing device using a remote sensing tool to detect a position of the subject;
    a first signal generator for generating a signal, and capable of transmitting the signal to the subject in situ; and
    a first signal analyzer for receiving and analyzing a signal induced from the subject in situ;
    wherein the subject adaptor is a clamp, and the remote sensing tool comprises:
       a see through window with a scale mounted on an upper cover of the clamp, and the scale located on a side of the see through window; and
       an opaque cover mounted on the upper cover of the clamp and near the see through window; and
    wherein the position of the subject is fixed by measuring the position of the subject using the scale.

11. The apparatus as claimed in claim 10, wherein the opaque cover is a sliding lid.

12. The apparatus as claimed in claim 10, wherein the first signal generator and the first signal analyzer are used as a pulsatile oxygenometer.

* * * * *